(12) United States Patent
Klein

(10) Patent No.: US 8,306,188 B2
(45) Date of Patent: Nov. 6, 2012

(54) METHOD AND DEVICE FOR THE ONLINE DETERMINATION OF THE ASH CONTENT OF A SUBSTANCE CONVEYED ON A CONVEYOR, AND DEVICE FOR CARRYING OUT SUCH AN ONLINE DETERMINATION

(75) Inventor: Albert Klein, Simmersfeld (DE)

(73) Assignee: Elisabeth Katz, Simmersfeld (DE)

( * ) Notice: Subject to any disclaimer, the term of this patent is extended or adjusted under 35 U.S.C. 154(b) by 409 days.

(21) Appl. No.: 11/919,332

(22) PCT Filed: Apr. 26, 2006

(86) PCT No.: PCT/EP2006/003839
§ 371 (c)(1),
(2), (4) Date: Sep. 30, 2009

(87) PCT Pub. No.: WO2006/117106
PCT Pub. Date: Nov. 9, 2006

(65) Prior Publication Data
US 2010/0303201 A1    Dec. 2, 2010

(30) Foreign Application Priority Data
Apr. 30, 2005  (DE) .......................... 10 2005 020 567

(51) Int. Cl.
*G01N 23/087* (2006.01)
*G01N 23/223* (2006.01)

(52) U.S. Cl. .............. 378/98.9; 378/46; 378/53; 378/54

(58) Field of Classification Search .................... 378/44, 378/45, 46, 47, 48, 49, 50, 51, 53, 54, 55, 378/56, 98.9, 207, 98.11
See application file for complete search history.

(56) References Cited

U.S. PATENT DOCUMENTS

| 4,090,074 A | * | 5/1978 | Watt et al. ...................... 378/88 |
| 4,359,639 A |   | 11/1982 | Wykes et al. |
| 4,486,894 A |   | 12/1984 | Page et al. |
| 4,539,649 A | * | 9/1985 | Michaelis et al. ............ 702/137 |
| 4,566,114 A | * | 1/1986 | Watt et al. ...................... 378/88 |
| 4,696,023 A | * | 9/1987 | Kuusi .............................. 378/46 |
| 4,815,116 A | * | 3/1989 | Cho ................................. 378/53 |

(Continued)

FOREIGN PATENT DOCUMENTS
GB    1065919    4/1967
(Continued)

OTHER PUBLICATIONS

M. Yazdi, S Esmaeilnia, "Dual-energy gamma-ray technique for quantitative measurement of coal ash in the Shahroud mine, Iran", International Journal of Coal Geology, vol. 55, No. 2, Aug. 2003, pp. 151-156(6).

*Primary Examiner* — Allen C. Ho
(74) *Attorney, Agent, or Firm* — Rabin & Berdo, P.C.

(57) ABSTRACT

A method for the online determination of the ash content of a substance conveyed on a conveying device, includes a first measurement for determining the mass per unit area of the substance and a second measurement for determining the mean atomic number of the atoms present in the substance. An additional X-ray fluorescence measurement is carried out.

24 Claims, 3 Drawing Sheets

U.S. PATENT DOCUMENTS

| | | | |
|---|---|---|---|
| 4,884,288 A * | 11/1989 | Sowerby | 378/51 |
| 5,506,406 A | 4/1996 | Kapp et al. | |
| 5,654,551 A * | 8/1997 | Watt et al. | 250/356.1 |
| 5,721,759 A * | 2/1998 | Raatikainen | 378/47 |
| 5,778,041 A * | 7/1998 | Chase et al. | 378/53 |
| 6,038,280 A * | 3/2000 | Rossiger et al. | 378/50 |
| 6,130,931 A * | 10/2000 | Laurila et al. | 378/45 |
| 6,324,251 B1 * | 11/2001 | Kuwabara | 378/48 |
| 6,345,086 B1 * | 2/2002 | Ferrandino et al. | 378/44 |
| 6,370,221 B2 * | 4/2002 | Kaiser et al. | 378/45 |
| 6,370,223 B1 * | 4/2002 | Gleason et al. | 378/58 |
| 6,398,408 B1 * | 6/2002 | Polkus | 378/207 |
| 6,402,373 B1 * | 6/2002 | Polkus et al. | 378/207 |
| 6,402,374 B1 * | 6/2002 | Boomgaarden | 378/207 |
| 6,421,415 B1 * | 7/2002 | Peczkis et al. | 378/46 |
| 6,459,760 B1 * | 10/2002 | D'Ambrosio | 378/43 |
| 6,567,496 B1 * | 5/2003 | Sychev | 378/57 |
| 6,600,805 B2 * | 7/2003 | Hansen | 378/53 |
| 6,816,571 B2 * | 11/2004 | Bijjani et al. | 378/57 |
| 7,376,215 B2 * | 5/2008 | Hofman | 378/53 |
| 7,580,505 B2 * | 8/2009 | Kang et al. | 378/57 |
| 7,646,851 B2 * | 1/2010 | Liu et al. | 378/98.9 |
| 7,664,225 B2 * | 2/2010 | Klein | 378/45 |
| 7,702,075 B2 * | 4/2010 | Wang et al. | 378/98.9 |
| 2004/0240606 A1 | 12/2004 | Laurila et al. | |

FOREIGN PATENT DOCUMENTS

GB 2223574 4/1990

\* cited by examiner

METHOD AND DEVICE FOR THE ONLINE DETERMINATION OF THE ASH CONTENT OF A SUBSTANCE CONVEYED ON A CONVEYOR, AND DEVICE FOR CARRYING OUT SUCH AN ONLINE DETERMINATION

BACKGROUND OF THE INVENTION

Field of the Invention

The invention relates to a method for the online determination of the ash content of a substance conveyed on a conveying means, as well as to a device for carrying out such a method.

The use of radiometric methods for the online analysis of materials that are conveyed on conveying belts, for example, is known in the field of mining and metallurgical engineering. One problem that may arise in this connection relates to the ash content of a substance, in particular the ash content of coke or coal. The so-called dual-energy method is known for determining this content. With this method, the substance to be measured is irradiated with two gamma rays or X-ray rays of different energy. For example, a $Cs^{137}$ source is used for the high-energy measuring section and an $Am^{241}$ source is used for the low-energy measuring section. The share of ash in the irradiated substance, for example coal, can then be computed on the basis of the difference in the absorption behavior of the two rays.

The method is based on the fact that the mass per unit area of the substance is determined with the aid of the absorption behavior of the high-energy ray and that additionally the mean atomic number of the atoms present in the substance can be determined with the aid of the absorption behavior of the low-energy ray. This method is a non-contacting method and be used for grain sizes up to and in special cases even exceeding 100 mm. It does not deliver satisfactory results in all cases.

SUMMARY OF THE INVENTION

Starting with this premise, it is the object of the present invention to create a method which makes it possible to improve the accuracy for the on-line determination of the ash content of a substance.

This object is solved with a method having the features as disclosed in claim 1.

It has turned out that the accuracy of the measuring results is frequently unsatisfactory in cases where the chemical composition of the ash changes. The result of the ash content determination is incorrect, especially if there is a change in the concentration of heavy elements such as calcium or iron, as well as the concentration of elements with a higher atomic number.

An X-ray fluorescence measurement is therefore additionally carried out according to the invention, which has a spectrum containing in particular the $K_\alpha$ lines of these elements. This information is subsequently utilized for correcting the measuring results. Owing to the fact that only the $K_\alpha$ radiation of relatively heavy elements must be measured, for which the energy is relatively high and which is not substantially disturbed by air absorption, the X-ray fluorescence measurement can be realized fairly easily from a measuring-technical point of view, and it is possible to have a relatively long distance between the X-ray fluorescence detector and the sample surface. A typical distance is approximately 20 cm from the substance surface.

The mass per unit area of the substance and the atomic number are preferably determined with the aid of a so-called dual energy measurement, mentioned in the above, for which the substance is irradiated with X-rays and gamma rays of differing energy.

The required X-ray fluorescence detector is preferably positioned on the same side of the sample as the exciting source, for which preferably one of the two sources for the dual energy measurement simultaneously functions as excitation source. With an arrangement of this type, the measuring results are always dependent on the geometry, which must either be compensated or the arrangement must be selected such that the same geometric conditions always result. An arrangement is disclosed wherein the source or the sources and the X-ray detector or the X-ray detectors are rigidly connected to a floating or gliding element. This element is arranged movable in such a way, relative to the conveying means, that it floats or glides on the conveyed substance. A device of this type is particularly suitable for the method proposed herein, but can conceivably be used for other applications as well.

The invention is explained in further detail with the aid of the exemplary embodiments, which show in:

DETAILED DESCRIPTION OF THE INVENTION

Figure 1:
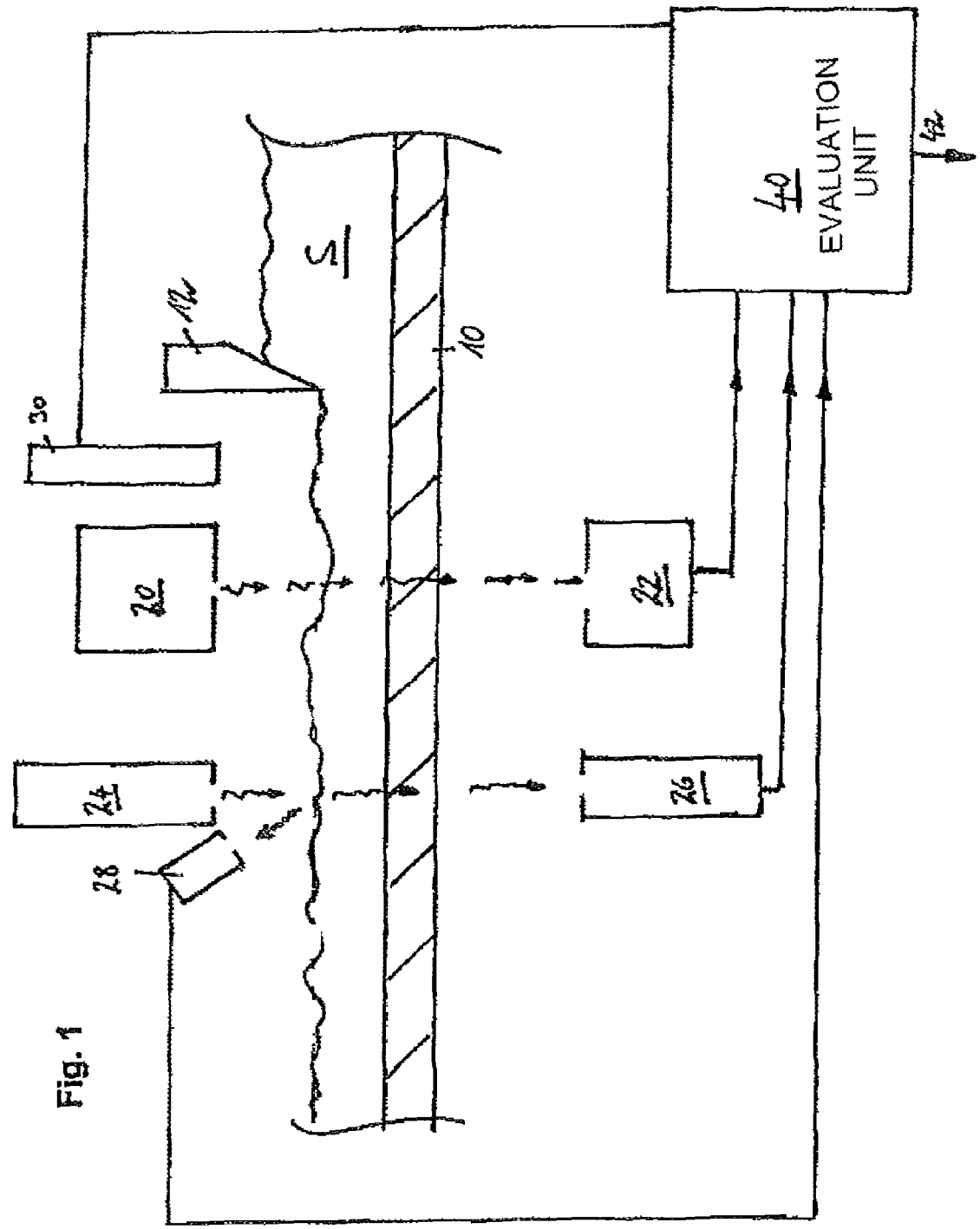
FIG. 1 A schematic representation of a device for carrying out the method according to the invention.

FIG. 1 schematically illustrates a device for the online determination of the ash content of the substance S conveyed on the conveyor belt 10. Initially, the substance S is leveled with the aid of the leveling plough 12, wherein a certain unevenness of the surface remains, depending on the granular consistency of the substance S.

Arranged above the conveyor belt 10 are a $Cs^{137}$ source 20, an $Am^{241}$ source 24, an X-ray fluorescence detector 28, as well as a distance meter 30 if applicable. The first transmission detector 22 and the second transmission detector 26 are located below the conveyor belt 10. The first transmission detector 22, the second transmission detector 26, the X-ray fluorescence detector 28 and, if applicable, the distance meter 30 are connected to the evaluation unit 40. This unit computes the ash content of the substance S, conveyed on the conveyor belt 10, by using the supplied measuring data and, if applicable, by using additionally stored calibration curves and subsequently releases the data via an output 42.

The $Cs^{137}$ source 20 and the first transmission detector 22 form the high-energy transmission measuring section, which is used for determining the mass per unit area of substance. In the process, the substance is irradiated from the top to the bottom, wherein a reverse configuration is also possible. The energy of the gamma radiation emitted by the $Cs^{137}$ source 20 is 660 keV (kiloelectron Volt). The $Am^{241}$ source 24 and the second transmission detector 26 form the low-energy transmission measuring section for determining the mean atomic number. The energy of the gamma radiation emitted by the $Am^{241}$ source 24 is 60 keV. These two sections form a "classic" dual-energy measuring arrangement for determining the ash content of the substance S, at least in principle. Instead of gamma sources, X-ray tubes with different accelerating voltages can also be used. The X-ray tube for the high-energy measuring section in this case should have an accelerating voltage of more than 300 kV while the X-ray tube for the low-energy measuring section should have an accelerating voltage of less than 100 kV.

The determination of the ash content with the aid of the data obtained in this way is known in the technical field, but will nevertheless be illustrated again briefly in the following:

The following absorption principle applies for the transmission of gamma rays:

$$I = I_0 e^{-\mu p d}$$

I: intensity
Io: intensity with empty measuring section
μ: absorption coefficient
p: density of the material
d: thickness of the material layer For low-energy rays, for example for the second transmission path with the $AM^{241}$ source, the absorption coefficient depends on the atomic number Z. The absorption coefficient of a mixture of substances can be displayed as follows:

$$\overline{\mu(z)} = \Sigma c_i \cdot \mu_i(z)$$

wherein $c_i$ is the concentration and
$\Sigma c_i = 1$.

For the classic dual-energy ash content measurement, the ash content A is measured according to the following formula:

$$A = \alpha \cdot \frac{ln\left(\frac{I}{I_o}\right)_{LE}}{ln\left(\frac{I}{I_o}\right)_{HE}} + k = \alpha \cdot \frac{(-\overline{\mu(z)} \cdot p \cdot d)_{LE}}{-\mu \cdot p \cdot d_{HE}} + k = \alpha \cdot \frac{\overline{\mu(z)}_{LE}}{\mu_{HE}} + k,$$

wherein
LE denotes the low-energy measuring section and HE the high-energy measuring section.

The letters α and k herein stand for the calibration coefficients. According to the invention, these coefficients are determined at least in part with an X-ray fluorescence measurement. This measurement is realized with the X-ray fluorescence detector 28, which preferably utilizes the excitation radiation of the $Am^{241}$ source 24. It is important for that reason that the $Am^{241}$ source 24 and the X-ray fluorescence detector 28 are located above the substance since the X-ray fluorescence measurement would otherwise be disturbed by the conveyor belt. In the process, the $K_O$ lines of several heavy elements such as calcium, iron and titanium are measured. The X-ray fluorescence radiation of interest herein is sufficiently rich in energy, so that the X-ray fluorescence detector 28 can be positioned at a distance of more than 10 cm, preferably approximately 20 cm, from the sample surface without the air absorption exerting too much influence. However, since the intensity of the fluorescence radiation decreases by the square of the distance, it is important to know the mean distance between the sample surface and the X-ray fluorescence detector 28. This can be achieved by keeping the distance constant or by continuously measuring the distance, for example with the aid of the distance meter 30. However, it is also possible to determine the layer thickness of the substance and, if the geometry is known, the distance from the sample surface to the individual measuring devices from the absorption behavior in the high-energy measuring section.

To keep the radiation intensity that impinges on the substance constant, even with a changing layer thickness for the substance S, an X-ray half-lens in the form of a collimator can be arranged between the $Am^{241}$ source and/or an X-ray tube replacing this source, and the substance S. In that case, the quadratic distance law need only be considered for the distance between the surface of the substance and the X-ray fluorescence detector, which can simplify the mathematical treatment.

As previously mentioned, some heavy elements are determined with the additionally carried out X-ray fluorescence measurement. These elements are calibrated as disclosed in the prior art. In the simplest case, the intensities of the peaks $I_{pi}$ can be taken as measure for the concentration, wherein the $k_i$ values are constants:

$$c_i = k_i I_{pi}$$

To compensate for the elementary composition of the ash, the mean elementary composition of the ash (operating point) is calibrated with the aid of the dual energy measurement. Deviations of the ash elements, detected with the X-ray fluorescence analysis, from the operating point are then compensated as follows:

$$A = \alpha \cdot \frac{ln\left(\frac{I}{I_o}\right)_{LE}}{ln\left(\frac{I}{I_o}\right)_{HE}} - \sum \mu_i \Delta c_i + k^*$$

In this case, $\Delta c_i$ is the deviation of the concentration of the element i from the mean value and k* is a constant.

If one uses the peak intensities instead of a calibrated X-ray fluorescence measuring section, which determines the concentration of the desired elements, then the calibration of the ash content measurement can occur with the aid of a total regression:

$$A = \alpha \cdot \frac{ln\left(\frac{I}{I_o}\right)_{LE}}{ln\left(\frac{I}{I_o}\right)_{HE}} + b_1 \Delta I_{p1} + b_2 \Delta I_{p2} + \ldots k^*$$

Since the X-ray fluorescence measuring section is not calibrated in this case, only the laboratory value of the ash content is needed for the calibration. The laboratory expenditure is therefore not higher than is already required for the dual-energy method.

The evaluation unit 40 carries out the calculation operations shown in the above.

As can be seen, the absolute intensities play a role for the X-ray fluorescence measuring. It is therefore extremely important to have a precise value for the distance between the sample surface and the X-ray fluorescence detector, ideally also for the distance between the $Am^{241}$ source and the sample surface, and to keep this distance constant. The distance can be measured for this and the value obtained for the measured distance can be used for the correction.

Figure 2:
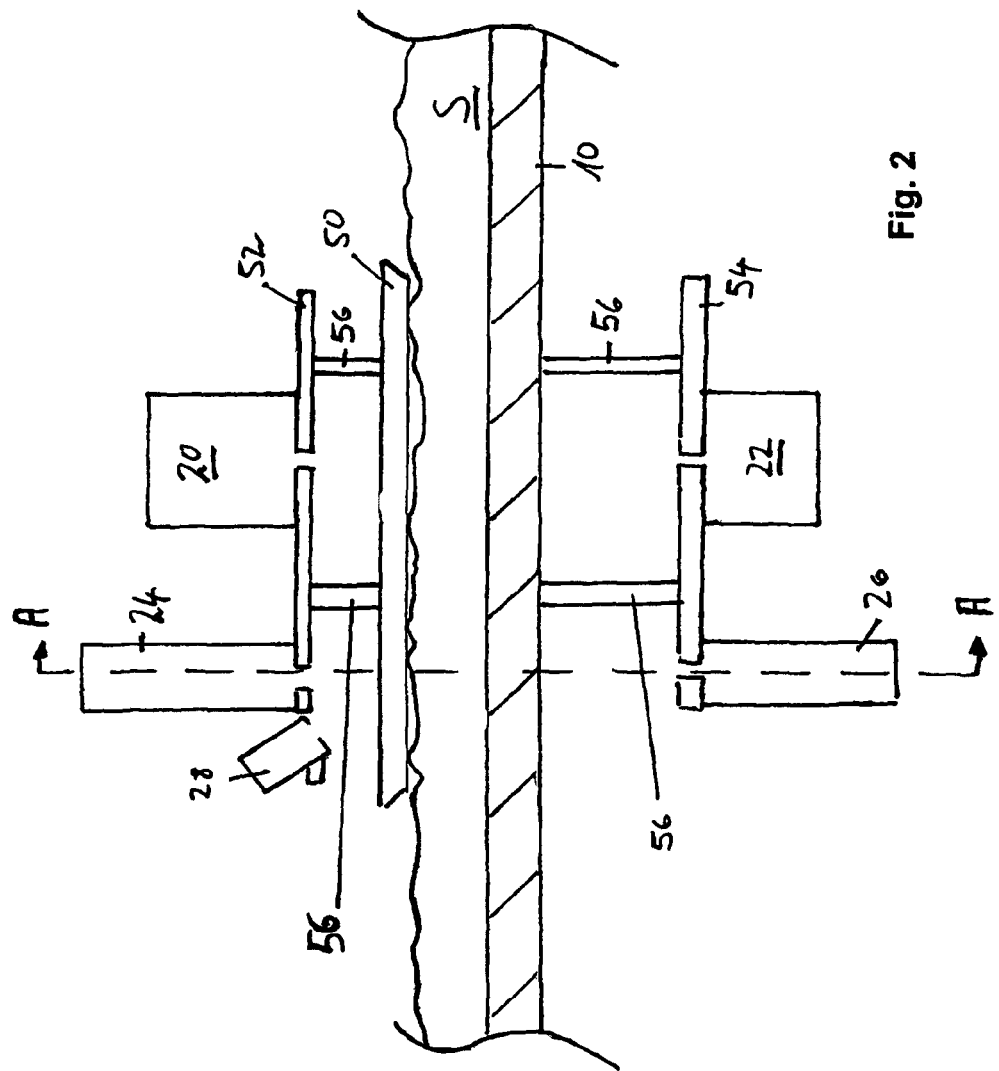
FIG. 2 A second embodiment of a device for carrying out the method according to the invention, shown in a schematic representation.
Figure 3:
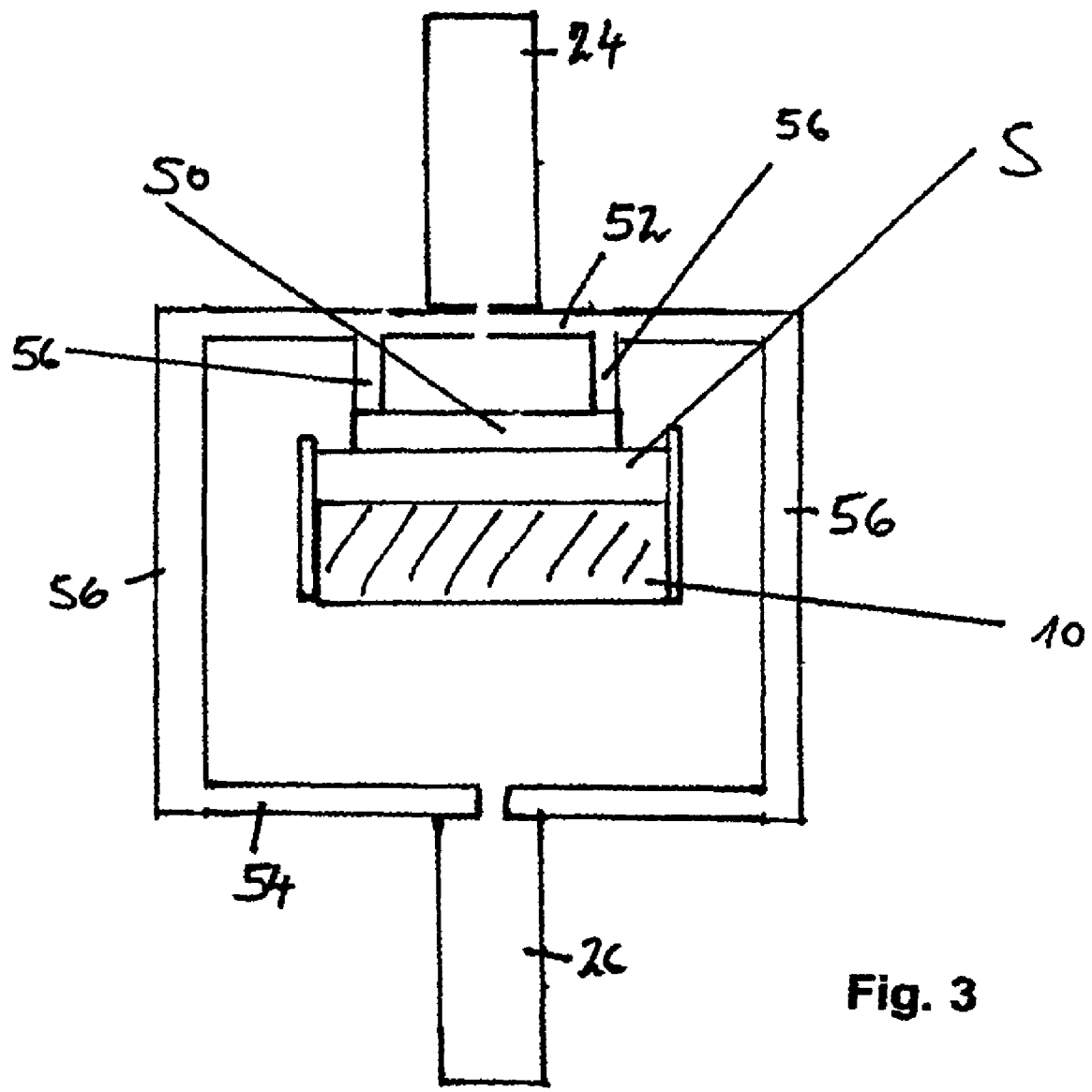
FIG. 3 A sectional view along the plane A-A in FIG. 2.

FIGS. 2 and 3 show one option for always keeping the distance constant, without this resulting in a negative influence on the two transmission measurements. The measuring device in that case has a gliding plate 50, which glides or swims along on the surface of the substance S to be measured. An upper fastening plate 52 and a lower fastening plate 54 are rigidly connected via supports 56 to this gliding plate 50. As a result, the distance between the $Cs^{137}$ source 20 and the first transmission detector 22, as well as the distance between the Am$^{241}$ source 24 and the second transmission detector 26 always remains the same. In addition, the distance also remains the same between the Am$^{241}$ source 24 and the sample surface, as well as between the sample surface and the X-ray fluorescence detector 28. Since the layer thickness of the substance S to be measured does not play a role for the dual-energy measurement as well as for the X-ray fluorescence measurement, this arrangement also ensures uniform measuring results if the layer thickness changes. An arrangement of this type, using a gliding or floating plate 50, can also be used for different applications using radiometric methods.

LIST REFERENCE NUMBERS 10 conveyor belt
12 leveling plough
20 Cs$^{137}$ source
22 first transmission detector
24 Am$^{241}$ source
26 second transmission detector
28 X-ray fluorescence detector
30 distance meter
40 evaluation unit
50 gliding plate
52 upper fastening plate
54 lower fastening plate

The invention claimed is:

1. A method for an online determination of an ash content of a substance conveyed on a conveyor, comprising:
   measuring a first measurement by irradiating a substance with high-energy X-ray or gamma ray radiation;
   determining a mass per unit area of the substance based on the first measurement;
   measuring a second measurement by irradiating the substance with low-energy X-ray or gamma ray radiation;
   determining a mean atomic number of the atoms present in the substance based on the second measurement;
   measuring an X-ray fluorescence; and
   using the X-ray fluorescence measurement to correct a result obtained by the first and the second measurements.

2. The method according to claim 1, wherein the substance is irradiated with high-energy X-ray or gamma ray radiation to determine the mass per unit area.

3. The method according to claim 2, wherein the high-energy gamma ray radiation is generated by a Cs$^{137}$ source.

4. The method according to claim 1, wherein the substance is irradiated with low-energy X-ray or gamma ray radiation for determining the mean atomic number.

5. The method according to claim 4, wherein the low-energy gamma ray radiation is generated by an Am$^{241}$ source.

6. The method according to claim 4, wherein the low-energy gamma ray or X-ray radiation also functions as excitation radiation for the X-ray fluorescence measurement.

7. The method according to claim 6, wherein an X-ray fluorescence detector is located on the same side of the substance as a source for the low-energy X-ray or gamma ray radiation.

8. The method according to claim 7, wherein a uniform distance is maintained between a surface of the substance and the source for the low-energy X-ray or gamma ray radiation, and the X-ray fluorescence detector.

9. The method according to claim 8, wherein the distance is furthermore kept constant between the source of the low-energy X-ray or gamma ray radiation, and a transmission detector for transmitted low-energy X-ray or gamma ray radiation.

10. The method according to claim 6, wherein a source of the low-energy X-ray or gamma ray radiation and a fluorescence detector are arranged at a fixed distance relative to the conveyor and that changes in a distance to a surface of the substance are technically measured and the effect on an X-ray fluorescence signal is mathematically corrected.

11. The method according to claim 10, wherein a transmission measurement of high-energy radiation is used for a distance measurement.

12. The method according to claim 10, wherein back-scattered radiation of the low-energy gamma ray or X-ray radiation is used for determining a mean density and/or a mass per unit area.

13. The method according to claim 12, wherein the substance is irradiated directly.

14. The method according to claim 13, wherein the distance between the source of the low-energy X-ray or gamma ray radiation and the detector to the surface of the substance is measured for measuring the back-scattered radiation and that a measuring result is used for mathematically correcting the result.

15. The method according to claim 12, wherein a distance from a source for the low-energy X-ray or gamma ray radiation, and a detector to a surface of the substance is kept constant for measuring back-scattered radiation.

16. The method according to claim 12, wherein a back-scattering signal and an X-ray fluorescence signal are detected by a joint detector and are then separated during an evaluation.

17. The method according to claim 4, wherein a distance between a source of the low-energy X-ray or gamma ray radiation and a transmission detector is measured, and the analysis of a transmission measurement is based on the measured distance.

18. The method according to claim 17, wherein the transmission measurement obtained for a high-energy radiation is used for a distance measurement.

19. The method of claim 1, wherein the X-ray fluorescence measurement is carried out by using an X-ray fluorescence detector being located at a distance of at least 10 cm from the surface of the substance.

20. A method for an online determination of an ash content of a substance conveyed on a conveyor, comprising:
   measuring a first measurement by irradiating a substance with high-energy X-ray or gamma ray radiation;
   determining a mass per unit area of the substance based on the first measurement;
   measuring a second measurement by irradiating the substance with low-energy X-ray or gamma ray radiation;
   determining a mean atomic number of the atoms present in the substance based on the second measurement;
   measuring an X-ray fluorescence;
   using the X-ray fluorescence measurement to correct a result obtained by the first and the second measurements;
   arranging a source of the low-energy X-ray or gamma ray radiation and a fluorescence detector at a fixed distance relative to the conveyor;
   technically measuring changes in a distance to a surface of the substance; and
   mathematically correcting the effect on an X-ray fluorescence signal.

21. A device for realizing a method for the online determination of the ash content of a conveyed substance, comprising:
   a first X-ray or gamma ray source with an associated first transmission detector;

a second X-ray or gamma ray source with an associated second transmission detector;
a conveyor configured to convey the conveyed substance;
an X-ray fluorescence detector; and
a gliding element,
wherein the first X-ray or gamma ray source, the first transmission detector, the second X-ray or gamma ray source, the second transmission detector and the X-ray fluorescence detector are rigidly connected to the gliding element, which is arranged movable with respect to the conveyor, such that the gliding element glides along the conveyed substance, and wherein the first X-ray or gamma ray source, the second X-ray or gamma ray source and the X-ray fluorescence detector are arranged above the conveyor and the first and the second transmission detector are arranged below the conveyor.

22. The device according to claim 21, further comprising an X-ray half lens that is arranged as a collimator between the second X-ray or gamma ray source and the substance.

23. The device according to claim 21, wherein the conveyor is a conveyor belt.

24. The device according to claim 21 wherein the conveyor is an open groove.

\* \* \* \* \*